Figure 1:
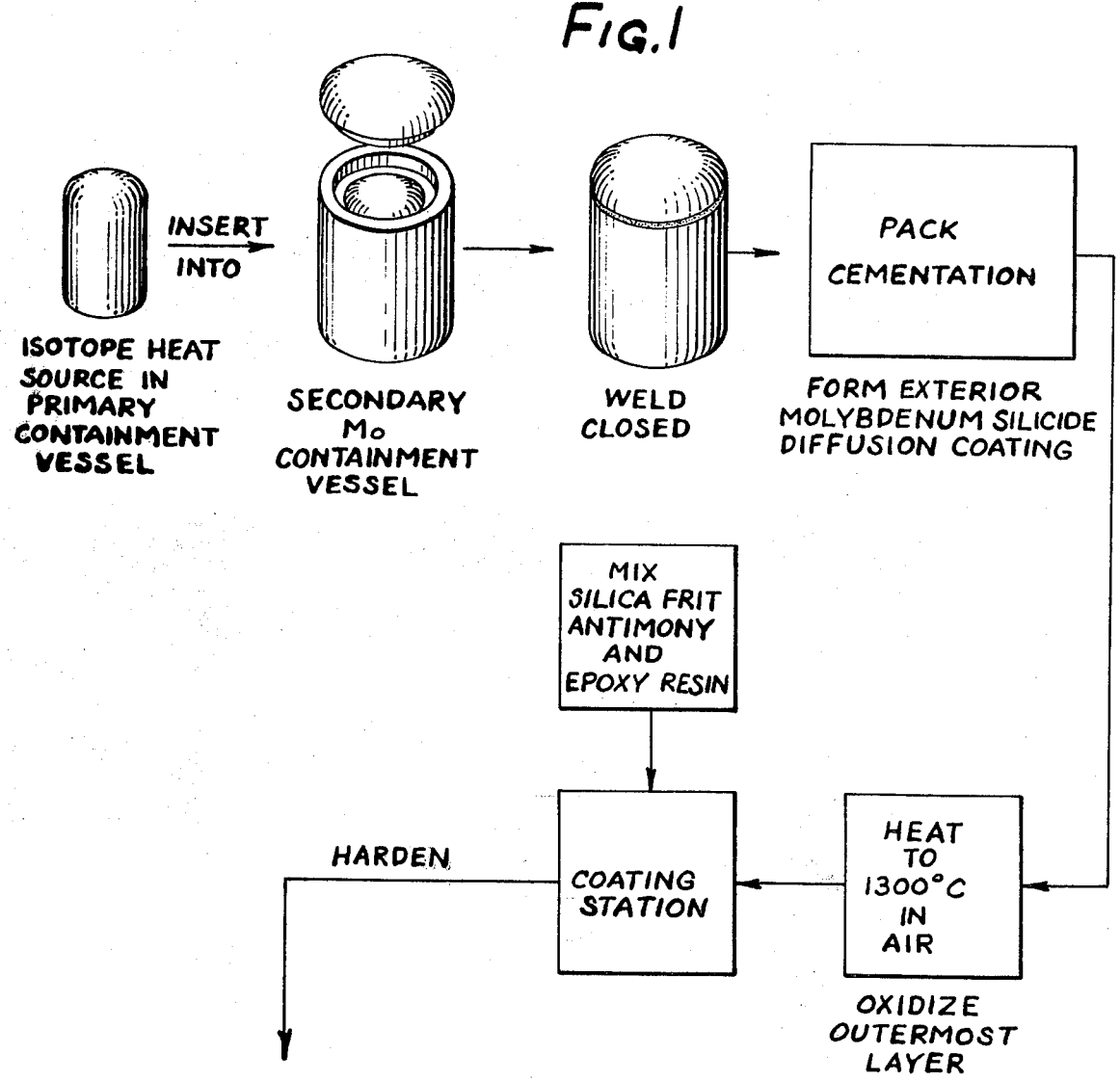

United States Patent [19]

Elsner

[11] 4,001,588
[45] Jan. 4, 1977

[54] RADIOACTIVE HEAT SOURCE AND METHOD OF MAKING SAME

[75] Inventor: Norbert Bernard Elsner, La Jolla, Calif.

[73] Assignee: General Atomic Company, San Diego, Calif.

[22] Filed: July 17, 1975

[21] Appl. No.: 517,877

[52] U.S. Cl. .............................. 250/493; 250/496
[51] Int. Cl.² ......................................... G21G 4/00
[58] Field of Search ........................... 250/493, 496

[56] References Cited

UNITED STATES PATENTS

| | | | |
|---|---|---|---|
| 3,533,913 | 10/1970 | Botts et al. | 250/493 X |
| 3,697,329 | 10/1972 | Bunker et al. | 250/496 X |
| 3,767,930 | 10/1973 | Sayell | 250/493 |

Primary Examiner—Archie R. Borchelt
Attorney, Agent, or Firm—Fitch, Even, Tabin & Luedeka

[57] ABSTRACT

A radioactive source of heat which is resistant to cremation conditions is made by encapsulating a radioisotope within a containment vessel and forming a refractory metal silicide diffusion coating exterior thereof. A secondary molybdenum vessel may be provided with a molybdenum silicide coating and then heated in air to oxidize its outer layer. A layer is applied exterior of the diffusion-coating which provides a continuous ceramic oxide layer upon subjection to cremation. This outer layer may be discrete silica carried in a hardenable binder of an organic polymer, and a minor amount of antimony is preferably also included.

13 Claims, 2 Drawing Figures

RADIOACTIVE HEAT SOURCE AND METHOD OF MAKING SAME

This invention relates to radioactive heat sources for use in nuclear batteries and the like, and more particularly to the providing protection for radioisotope heat sources for use in thermoelectric batteries which are designed for implantation within human beings in order to prevent destruction of the radioisotope containment vessel under usual cremation conditions.

More and more individuals are having pacemakers implanted within their bodies which are powered by small nuclear batteries. Moreover, as medical science progresses, there will likely be additional implantable devices which will utilize such nuclear batteries. These batteries generally utilize thermoelectric materials, such as bismuth telluride, which generates electricity as a result of the application of heat to one end thereof. The source of the heat is commonly a radioactive isotope which produces heat as a product of its constant radioactive decay and generally plutonium-238 is employed because of its availability.

Pu-238 is encapsulated within a strong primary containment vessel of a suitable metal alloy. Commonly, a containment vessel made of an alloy of tantalum and tungsten may be used, which alloy exhibits sufficient strength to retain the pressure build-up that occurs as a result of the creation of helium as a part of the decay process of plutonium-238. One example of such an implantable battery incorporating a containment vessel and a thermoelectric unit is described in U.S. Pat. No 3,781,176, issued Dec. 25, 1973 to Alan Penn et al. Obviously, it is important that the radioactive plutonium and any radioactive fission products of the plutonium decay be confined. There is generally no problem in maintaining effective containment under normal conditions; however, it is becoming more common for bodies to be cremated after death. Cremation conditions (for example, heating to about 1300° C. under oxidizing conditions for 2 hours) may result in the rupture and/or destruction of the containment vessel and in consequent radioactive contamination from the plutonium isotope source and the decay products thereof. Solutions to this problem of potential destruction during cremation are needed inasmuch as conditions may arise in which a nuclear battery is not removed from a body prior to cremation.

It is an object of the present invention to provide an improved radioactive heat source for use in a nuclear battery which will resist destruction when subjected to cremation conditions. It is another object of the invention to provide a method for making a radioactive heat source for use in a nuclear battery which will be resistant to destruction upon exposure to cremation conditions. A further object of the invention is to provide a nuclear battery for implantation in the human body which is constructed so as to avoid spreading radioactive contamination upon cremation of the corpse in which it is implanted. Still another object of the invention is to provide a nuclear battery which includes a thermoelectric generator, plus a heat source in the form of a radioactive isotope, which heat source is protected so as to maintain its integrity although the battery is subjected to cremation conditions.

These and other objects of the invention will be apparent from the following description of the methods for making radioactive heat sources for use in nuclear batteries embodying various features of the invention. For purposes of this application, the terminology "nuclear battery" should be understood to mean the assemblage of a thermoelectric unit, plus a radioactive heat source, having an overall size suitable for implantation in the human body which assemblage is designed to provide a relatively constant output of electric power.

It has been found that the usual primary containment vessel in which a radioisotope heat source is encapsulated can be protected from breach and/or destruction when subjected to cremation conditions by providing a secondary containment vessel of refractory metal which is in turn itself suitably protected. In this respect, the refractory metal is provided with an exterior diffusion coating, as by using a pack diffusion process or the like, of the refractory metal silicide which is high temperature stable. On the outer surface of the diffusion-coated refractory metal, there is disposed a layer of ceramic-oxide-containing material which will provide a relatively inert protective film under cremation conditions.

Figure 2:
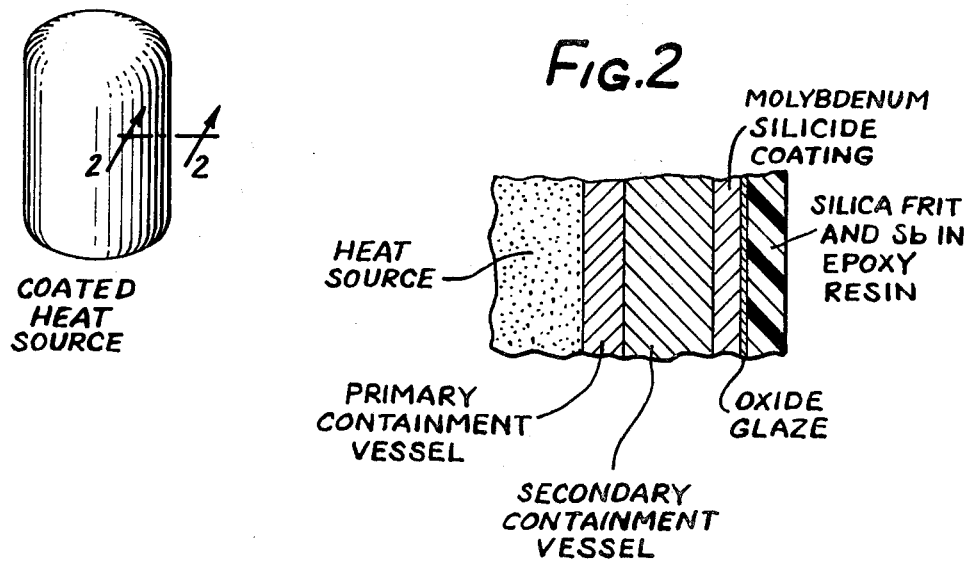

A representative method for forming a protected heat source is diagrammatically depicted in the drawings wherein:

FIG. 1 shows a method for coating an isotope heat source embodying various features of the invention, and FIG. 2 is an enlarged, fragmentary, sectional view of the coated heat source which results from the method depicted in FIG. 1.

The radioactive isotope that is commonly employed is plutonium-238, which decays by the emission of alpha particles and thus does not require extensive shielding and which has a relatively long half-life of 89 years. Although other radioisotopes might be employed, for example curium-244, which is also an alpha-emitter and has a half-life of about 18 years, plutonium-238 is preferred. The radioisotope is encapsulated within a strong primary containment vessel, and the composite of radioisotope plus containment vessel is usually referred to as the fuel capsule. Various types of strong and chemically resistant metal alloys have been used for the primary containment vessel in making fuel capsules. Hastelloy-C and Hastelloy-X, which are alloys having a major portion of nickel and minor portions of molybdenum, chromium, iron and cobalt may be used. More recently, alloys of tantalum and tungsten have become available which are presently preferred because they provide high strength and chemical inertness.

The usual implantable nuclear battery utilizes an array of thermoelectric generating modules to convert the heat, which is produced in the fuel capsule to electricity. Examples of such thermoelectric generating arrays are described in U.S. Pat. Nos. 3,780,425 and 3,781,176 which issued on Dec. 25, 1973. The alpha particles given off during the Pu-238 decay process are absorbed in the metal alloy of the primary containment vessel where the kinetic energy of the alpha particles is turned into heat raising the temperature of the primary containment vessel. The alpha particle remains as a helium atom, gradually increasing the pressure within the fuel capsule, and the primary containment vessel must be designed to withstand such increasing internal pressure.

The heat from the fuel capsule is transferred to the hot junction of the thermoelectric modules, resulting in the generation of electrical power therein, which in the usual pacemaker battery is less than 20 milliwatts. Commonly, the fuel capsule and the thermoelectric generating modules are disposed within a suitable enclosure through which leads for the conduction of electrical current extend.

Plutonium is poisonous, and from a safety standpoint, it must be assured that the primary containment vessel will not be breached lest plutonium be dispersed to living organisms. Under normal conditions, and particularly in view of the minute size of the fuel capsule, ample protection is provided by the metal alloy containment vessel so that there is no hazard during an implantation in a human body. However, when cremation of a corpse occurs wherein such a battery is implanted, the conditions to which the fuel capsule will be subjected must be taken into consideration.

Under some conditions, cremation may be carried out at a maximum temperature of about 1300° C. for a time of about 2 hours. In addition to preventing oxidation of the metal alloy primary containment vessel under such maximum temperature conditions, the potential reaction of the alloyed metals with other components of the thermoelectric battery system must be taken into consideration. The thermoelectric modules may employ materials such as suitably doped bismuth telluride or lead telluride or the like, and copper and other materials for contacts and wiring connections will also be present. The potential interaction of these materials at temperatures of about 1300° C. must be considered.

It has been found that oxidation protection can be provided by employing an oxidation-resistant layer of refractory metal silicide. If a Ta—W alloy is used for the primary containment vessel, the silicide coating may be formed directly upon the outer surface thereof. However, double-containment systems provide a certain sense of security for holding radioactive materials and the use of a refractory metal secondary containment vessel is preferred. Such a secondary vessel is preferably made of molybdenum or an alloy which constitutes at least about 75 percent Mo. Other refractory metals which may be used include tantalum, tungsten, niobium and suitable alloys containing at least about 75 weight percent thereof.

Refractory metal silicides provide good high-temperature oxidation resistance, and the refractory metal is treated to form a silicide diffusion coating on the outer surface thereof. A suitable silicon-pack-diffusion treatment is preferably employed, which is sometimes referred to as pack cementation; however, other methods of forming a diffusion coating may also be used, for example vacuum vapor deposition or chemical vapor deposition, as by high-temperature decomposition of silane or a like compound. In this process, silicon diffuses into the outer surface of the refractory metal secondary containment vessel so as to form an exterior layer at least about 1 mil (0.025 mm.) in depth, which may be up to about 3 to 5 mils, that is predominantly refractory metal silicides. Usually, refractory metals form compounds with silicon in different proportions, and when molybdenum is used, the diffusion coating may comprise a mixture of $MoSi_2$, $Mo_5Si_3$ and $Mo_3Si$. After the diffusion coating process is completed, heating in air at a temperature of about 1300°C. for at least about 30 minutes is carried out to oxidize the outermost molecular layer of the diffusion-coating. As a result, a thin, white continuous crust appears over the surface of the molybdenum silicide coating which is substantially pure silicon dioxide.

The oxidized refractory metal silicide diffusion coating will adequately protect the fuel capsule from oxidation over the usual period of cremation; however, the possibility remains that there may be chemical attack of the refractory metal silicides by other components in the battery, for example, the bismuth telluride, if the temperature approaches 1300° C. To shield the diffusion coating against such potential chemical attack, an outer barrier which contains a ceramic oxide, preferably silica is employed. Other ceramic oxides which may be used include alumina, zirconia, titania, yttria and hafnia. The barrier may be substantially totally ceramic oxide; for example, a silica or other ceramic oxide coating may be applied by flame-spraying or plasma-spraying or the like, or by disposing the fuel capsule within a thin quartz tube which is subsequently melted and fused onto the outer surface of the secondary containment vessel. However, from a manufacturing standpoint and from a performance standpoint, it is preferred that an organic polymer having relatively good heat conduction properties and having a very low vapor pressure at the operating temperature is used as a binder for holding the ceramic oxide in particulate form, preferably particles of silica frit or quartz fibers. By choosing a polymeric resin having good heat-conduction, an undesirable large heat loss across this protective barrier is avoided and significant production advantage is obtained. During cremation, the organic polymer will be degraded and to some extent oxidized under conditions which will cause the silica frit particles or quartz fibers to sinter together and form a continuous silica barrier concurrent with the degradation of the polymer.

So as to assure that there is sufficient ceramic oxide to form a continuous barrier, the frit of fibers should constitute at least about 30 weight percent of the exterior barrier layer and preferably constitutes between about 30 and about 50 weight percent. The size of frit particles is preferably between about 100 mesh (0.147 mm.) and about 200 (0.074 mm.). If fibers are used, the diameter of the fibers is preferably between about 0.1 mm. and about 0.2 mm.

The preferred polymer is an epoxy resin which exhibits good high-temperature stability (and accordingly a low vapor pressure at the normal fuel capsule operating temperature, i.e., about 75° C.). Suitable epoxy resins include the most widely used types, which are diglycidyl ethers of Bisphenol A, as well as epoxy novolac resins and epoxy phenol-novolac resins. Mineral-and-metal-filled epoxy resins may be used to improve thermal conductivity so long as the fillers do not have chemical properties that would react with the diffusion-coated secondary containment vessel at cremation conditions. Examples of other organic polymers which might be employed include polytetrafluroethylene, melamine-formaldehyde resins, phenol-formaldehyde resins, phenol-furfural resins, polyesters and urea-formaldehyde resins.

Another advantage of using discrete material in an organic binder is that it facilitates inclusion in the outer barrier layer of a minor amount of antimony. The presence of antimony has been found to enhance the resistance of the silicide coating to molten metal attack on the refractory metal diffusion coating during cremation by improving the resistance of the coating to spalling, crazing and cracking. The inclusion of antimony in an amount of at least about 0.5 weight percent of the organic binder exhibits improvement; and it is preferably used at a level of between about 1 and 2 weight percent. Cracking of the silicide coating on the refractory metal secondary containment vessel is not a problem at normal operating conditions, and the potential exists only when cremation conditions occur. Under these conditions, it is believed that the presence of antimony helps quickly heal minor cracks which may occur by providing glass-forming oxides and serving as a sintering aid at the local region of immediate crazing, thus maintaining the thin silicon dioxide protective crust in a state of good repair.

The following example illustrates the best mode presently contemplated by the inventor for carrying out the invention; however, it should be understood that the example is only illustrative and does not constitute limitations upon the scope of the invention which is defined by the appended claims.

EXAMPLE

A fuel capsule is provided which includes about 180 milligrams of plutonium-238 disposed in a capsule of a tantulum-tungsten alloy having a wall thickness of about 1.5 mm. The Ta-W capsule is shaped as a cylinder having generally hemispherical ends with a diameter of about 8 mm. and a total height of about 15 mm. A sleeve of molybdenum metal about 6 mm. thick, and dimensioned to have a sliding-fit, is disposed about the fuel capsule, and close-fitting end caps are welded to the ends thereof to provide a secondary-containment vessel.

A powder mixture is prepared suitable for forming a silicide diffusion coating. The powder mixture is made up of about 18 weight percent silicon (particle size between about 50 mesh (0.3 mm.) and about 100 mesh (0.15 mm.), aluminum oxide, as an inert diluent, in an amount of about 80 weight percent (particle size between about 0.3 mm. and 0.04 mm.) and sodium fluoride reagent-grade powder, as an activator, in an amount of about 2 weight percent (particle size between about 0.15 mm. and 0.075 mm.). The molybdenum metal-clad fuel capsule is placed within a quartz tube, together with a sufficient amount of this powder mixture to constitute a pack diffusion or cementation bed that will blanket the entire surface thereof. The quartz tube is then outgassed under vacuum for about 1 hour and is then sealed. Heating is then carried out for about 16 hours at 975° C. After slowly cooling, the clad fuel capsule is removed from the tube, examined and found to have a diffusion coating to a depth of about 0.002 inch (0.05mm.), in the form of molybdenum silicides.

The diffusion-coated capsule is cleaned and then heated in air at about 1300° C. for about 40 minutes. After cooling, examination shows that a slight glaze has formed about the cladding. The glaze material is found to constitute silicon dioxide which has been formed by the oxidation of the molybdenum silicides in the surface region.

A mixture for coating is then formed of an epoxy resin plus silica frit. The mixture is formed from 54 parts by weight of epoxy resin (Epon 828, a product of the Shell Oil Company), 6 parts of hardener (DTA, a product of the Shell Oil Company), 38 parts of silica frit having a particle size between about 0.075 and about 0.15 mm. and 2 parts of antimony. A coating of about 25 mils thick of the epoxy-silica mixture is applied to the exterior of the clad fuel capsule, and the epoxy resin is hardened at a temperature of about 100° C. for 4 hours.

Testing of the fuel capsule shows that the heat conduction of the multiple cladding is sufficiently good so that the exterior temperature measures about 75° C. which is considered to be fully acceptable for use in a nuclear battery which uses a thermoelectric conversion system.

A nuclear battery is assembled using the clad and coated fuel capsule, together with thermoelectric modular arrays employing bismuth telluride semiconductor materials alloyed with selenium and with antimony. The battery is encased within an enclosure of Type 304 stainless steel and forms an object about 0.6 inch (15.2 mm.) in diameter having a length of about 1.5 inch (38 mm.). Testing over a period of several weeks shows that the battery produces about 500 microwatts of electrical power.

To simulate cremation conditions for qualification testing, the entire battery is heated in air to a temperature of 1300° C. for 2 hours. After cooling, subsequent examination shows that the epoxy binder material has charred and decomposed while the silica frit contained therewithin has fused to form a continuous layer which encompasses the secondary containment vessel. Examination of the molybdenum cladding with its molybdenum silicide exterior coating shows that it remains substantially crackfree, and there is no evidence of any substantial chemical attack by bismuth, tellurium, copper, iron or any other of the other elements present within the battery. The fuel capsule retains its integrity, and there is no release of plutonium. The clad fuel capsule is considered to be excellently suited for use within an implantable nuclear battery that can be subjected to cremation without danger of plutonium contamination.

Although the invention has been described with regard to certain preferred embodiments, it should be understood that modifications as would be obvious to one having the ordinary skill in the art are intended to fall within the scope of the invention which is defined solely by the claims appended hereto. Various additional features of the invention are set forth in the claims that follow.

What is claimed is:

1. A radioactive source of heat which is suitable for use as a part of a nuclear battery for implantation in a human being, which source comprises
   a radioactive isotope,
   a containment vessel encapsulating said isotope and having sufficient strength to contain any gaseous products of radioactive decay,
   a high-temperature-resistant diffusion coating layer which is formed predominantly of refractory metal silicides disposed exterior of said containment vessel, and
   an outer layer of ceramic oxide material disposed exterior of said diffusion coating layer, which outer layer provides a substantially continuous ceramic oxide layer upon exposure to high-temperature oxidizing conditions and thereby protects said containment vessel.

2. The invention in accordance with claim 1 wherein a second vessel formed predominantly of molybdenum surrounds said containment vessel and a molybdenum silicide diffusion coating is formed on the outer surface of said second vessel.

3. The invention in accordance with claim 1 wherein said outer layer is formed of discrete ceramic oxide material held together by a binder of organic polymeric material, said ceramic oxide being present in an amount equal to at least about 30 weight percent of said exterior layer.

4. The invention in accordance with claim 3 wherein said polymeric binder which is employed contains at least about 0.5 weight percent antimony.

5. The invention in accordance with claim 4 wherein said organic material is an epoxy resin.

6. A method of making a radioactive source of heat which is resistant to cremation conditions, which method comprises
   providing a radioisotope encapsulated within a containment vessel,
   forming a high-temperature-resistant refractory metal silicide diffusion coating exterior of said containment vessel, and
   applying a ceramic oxide material layer exterior of said diffusion-coating which material provides a continuous ceramic oxide layer that protects said vessel upon subjection to cremation conditions.

7. A method in accordance with claim 6 wherein said diffusion-coated vessel is heated under oxidizing conditions to form a silicon dioxide layer upon the outer surface of said diffusion coating by oxidizing said refractory metal silicide.

8. A method in accordance with claim 7 wherein said containment vessel is surrounded with a secondary vessel made of at least a major portion molybdenum and upon which a diffusion coating of molybdenum silicide is formed.

9. A method in accordance with claim 8 wherein said diffusion is carried out in a packed bed.

10. A method in accordance with claim 6 wherein said outer layer is formed by applying discrete ceramic oxide material mixed in a hardenable binder of organic polymeric material, said ceramic oxide material being present in sufficient amount to form a continuous protective film upon exposure to cremation conditions which cause degradation of said polymer.

11. A method in accordance with claim 10 wherein said polymeric binder which is employed contains at least about 0.5 weight percent antimony.

12. A method in accordance with claim 11 wherein said silica particles in an amount of at least about 30 weight percent of said outer layer are contained in said hardenable binder mixture.

13. A method in accordance with claim 6 wherein said outer ceramic oxide material layer is provided by disposing a quartz shell about said diffusion-coated vessel and heating to fuse said quartz onto said diffusion-coated exterior surface.

* * * * *